United States Patent
Daenen et al.

(10) Patent No.: US 9,539,197 B2
(45) Date of Patent: *Jan. 10, 2017

(54) HAIR CARE POLYMER

(71) Applicant: DSM IP ASSETS B.V., Heerlen (NL)

(72) Inventors: Robin Elisabeth Maria Jacobus Daenen, Basel (CH); Franciscus Johannes Marie Derks, Basel (CH); Dirk Weber, Basel (CH); Ruediger Wilz, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/424,651

(22) PCT Filed: Aug. 12, 2013

(86) PCT No.: PCT/EP2013/066826
§ 371 (c)(1),
(2) Date: Feb. 27, 2015

(87) PCT Pub. No.: WO2014/040811
PCT Pub. Date: Mar. 20, 2014

(65) Prior Publication Data
US 2015/0216789 A1    Aug. 6, 2015

(30) Foreign Application Priority Data

Sep. 17, 2012 (EP) .................... 12184655

(51) Int. Cl.
| | | |
|---|---|---|
| C11D 1/02 | (2006.01) | |
| C11D 1/88 | (2006.01) | |
| C08G 69/48 | (2006.01) | |
| A61Q 5/02 | (2006.01) | |
| A61K 8/88 | (2006.01) | |
| C08G 83/00 | (2006.01) | |
| C08L 101/00 | (2006.01) | |
| A61K 8/81 | (2006.01) | |

(52) U.S. Cl.
CPC ............. *A61K 8/88* (2013.01); *A61K 8/8164* (2013.01); *A61Q 5/02* (2013.01); *C08G 69/48* (2013.01); *C08G 83/006* (2013.01); *C08L 101/005* (2013.01); *A61K 2800/544* (2013.01)

(58) Field of Classification Search
CPC ........... C11D 1/02; C11D 1/88; C11D 3/3769; C08G 83/006; C08G 69/48; A61Q 5/02; A61K 8/8164; A61K 8/88; A61K 2800/544

See application file for complete search history.

(56) References Cited

U.S. PATENT DOCUMENTS

| | | | |
|---|---|---|---|
| 4,009,256 A | 2/1977 | Nowak et al. | |
| 2002/0165103 A1* | 11/2002 | Tsaur | A61K 8/73 510/130 |
| 2010/0069601 A1* | 3/2010 | Baumer | A61K 8/88 528/322 |

FOREIGN PATENT DOCUMENTS

| | | |
|---|---|---|
| CN | 102065833 | 5/2011 |
| WO | WO 2007/098888 | 9/2007 |
| WO | WO 2009/153334 | 12/2009 |

OTHER PUBLICATIONS

International Search Report for PCT/EP2013/066826 mailed Sep. 13, 2013.

* cited by examiner

*Primary Examiner* — Brian P Mruk
(74) *Attorney, Agent, or Firm* — Nixon & Vanderhye P.C.

(57) ABSTRACT

The invention relates to specific quaternized hyperbranched polymers having end-groups of formula (I) characterized in that said quaternized hyperbranched polymer is obtainable by preparation of a hyperbranched polymer having dimethylamino end groups by condensation of 2-dodecen-1-ylsuccinic anhydride, diisopropanolamine and N,N-bis[3-(dimethylamino)propyl]amine followed by quaternization of the dimethylamino end-groups to end groups of formula (I). Furthermore, the invention is directed to clear shampoo preparations comprising such quaternized hyperbranched polymers.

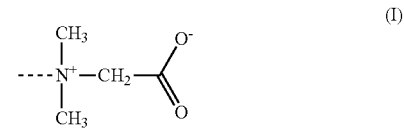

(I)

16 Claims, No Drawings

HAIR CARE POLYMER

This application is the U.S. national phase of International Application No. PCT/EP2013/066826, filed 12 Aug. 2013, which designated the U.S. and claims priority to EP 12184655.4, filed 17 Sep. 2012, the entire contents of each of which are hereby incorporated by reference.

The invention relates to specific quaternized hyperbranched polymers having end-groups of formula (I)

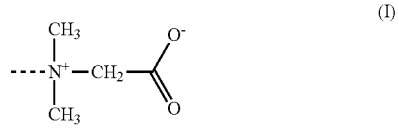

characterized in that said quaternized hyperbranched polymer is obtainable by preparation of a hyperbranched polymer having dimethylamino end groups by condensation of 2-dodecen-1-ylsuccinic anhydride, diisopropanolamine and N,N-bis[3-(dimethylamino)propyl]amine followed by quaternization of the dimethylamino end-groups to end groups of formula (I). Furthermore, the invention is directed to clear shampoo preparations comprising such quaternized hyperbranched polymers.

The use of quaternized or protonated hyperbranched polymers in hair care compositions is known from WO 2007/098888 A1. These polymers can be used as conditioning agents, strengthening agents, film forming agents, surfactants, anti-static agents, moisturizers, emulsifiers or hair styling agents. However, even though this polymer class exhibits excellent hair care benefits, many of them render shampoo preparations turbid making the use of a pearling agent mandatory in order to mask any turbidity in the final product. Furthermore, based on the monomers and reactants used the hyperbranched polymers are not easily accessible in high purity or a cosmetically acceptable color.

Thus there is an ongoing need for quaternized hyperbranched polymers suitable for the preparation of clear hair care compositions such as clear shampoos preparations making the use of a pearling agent obsolete. Furthermore such hair care compositions should exhibit a good viscosity in order to enhance the consumer acceptance. In addition such quaternized hyperbranched polymers should be directly accessible in high purities and a cosmetically acceptable color (colorless to light yellow or slightly brownish).

Surprisingly it has been found that quaternized hyperbranched polymers obtainable by condensation of 2-dodecen-1-ylsuccinic anhydride, diisopropanolamine and N,N-bis[3-(dimethylamino)propyl]amine followed by quaternization of the dimethylamino end-groups of the resulting hyperbranched polymer with sodium 2-chloroacetate allow the formulation of clear shampoo preparations. Incorporation of these quaternized hyperbranched polymers into standard shampoo formulations furthermore leads to excellent viscosities of the final product. In addition the condensation reaction of 2-dodecen-1-ylsuccinic anhydride, diisopropanolamine and N,N-bis[3-(dimethylamino)propyl] amine proceeds smoothly yielding hyperbranched polymers in high purity and an excellent color (slightly yellow brownish).

Thus, in one embodiment, the invention relates to quaternized hyperbranched polymers having end-groups of formula (I)

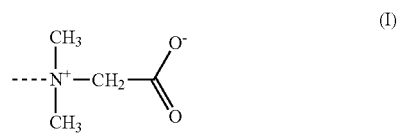

characterized in that said quaternized hyperbranched polymer is obtainable by
(i) preparation of a hyperbranched polymer having dimethylamino end groups by condensation of 2-dodecen-1-ylsuccinic anhydride, diisopropanolamine and N,N-bis[3-(dimethylamino)propyl]amine followed by
(ii) quaternization of the dimethylamino end-groups to end groups of formula (I).

Furthermore, the invention relates to a process for the preparation of a hyperbranched polymer having end-groups of formula (I) said process comprising the steps of
(i) preparation of a hyperbranched polymer having dimethylamino end-groups by subjecting 2-dodecen-1-ylsuccinic anhydride, diisopropanolamine and N,N-bis[3-(dimethylamino)propyl]amine to a condensation reaction followed by
(ii) quaternization of the dimethylamino end-groups to end groups of formula (I)

In a particular embodiment the hyperbranched polymers having dimethylamino end-groups are obtainable by condensation of 40-70 wt.-% of 2-dodecen-1-ylsuccinic anhydride, 5-20 wt.-% of diisopropanolamine and 15-45 wt.-% of N,N-bis[3-(dimethylamino)propyl]amine, in particular of 45-65 wt.-% of 2-dodecen-1-ylsuccinic anhydride, 8-18 wt.-% of diisopropanolamine and 20-40 wt.-% of N,N-bis[3-(dimethylamino)propyl]amine, most in particular of 55-65 wt.-% of 2-dodecen-1-ylsuccinic anhydride, 12-17 wt.-% of diisopropanolamine and 20-30 wt.-% of N,N-bis[3-(dimethylamino)propyl]amine, with the proviso that the total amount of 2-dodecen-1-ylsuccinic anhydride, diisopropanolamine and N,N-bis[3-(dimethylamino)propyl]amine sums up to 100 wt.-%.

The terms 2-dodecen-1-ylsuccinic anhydride (CASNo. [19780-11-1]), diisopropanolamine (CASNo. [110-97-4]) and N,N-bis[3-(dimethylamino)propyl]-amine (CASNo. [6711-48-4]) as used herein refers to pure 2-dodecen-1-ylsuccinic anhydride, diisopropanolamine and N,N-bis[3-(dimethylamino)propyl]-amine as well as to commercially available grades thereof. Such commercially available grades may contain a certain amount of impurities (commercially available technical grades) which preferably the should not exceed 15 wt.-%, more preferably 10 wt. % and most preferably 5 wt.-%.

2-Dodecen-1-ylsuccinic anhydride suitable for the purpose of the present invention is e.g. commercially available at Vertellus Chemiclas (Antwerpem, Belgium).

Suitable Diisopropanolamine for the purpose of the present invention is e.g. commercially available as Diisopropanolamine at BASF.

Suitable N,N-bis[3-(dimethylamino)propyl]amine for the purpose of the present invention is e.g. available at Huntsman Holland (Rotterdam, The Netherland as Tetramethyl iminobispropylamine).

In all embodiments of the present invention, it is preferred that the quaternized hyperbranched polymers having end groups of formula (I) are obtained by
(i) preparation of a hyperbranched polymer having dimethylamino end groups by condensation of 2-dodecen- 1-ylsuccinic anhydride, diisopropanolamine and N,N-bis[3-(dimethylamino)propyl]amine followed by (ii) quaternization of the dimethylamino end-groups to end groups of formula (I) with all the preferences and definition given herein.

In all embodiments of the present invention it is furthermore preferred that the quaternization is carried out using sodium 2-chloroacetate (CASNo. [3926-62-3]).

The amount (mol %) of dimethylamino end-groups in the hyperbranched polymers depends on the ratio of the building blocks i.e. 2-dodecen-1-ylsuccinic anhydride, diisopropanolamine and N,N-bis[3-(dimethylamino)propyl]amine and can easily be calculated and adjusted by a person skilled in the art. Dependent on the ratio of the building blocks, the hyperbranched polymers having diemethylamino end-groups may further comprise —OH or —COOH end-groups. Preferably, the ratio of the building blocks is selected such that 50 to 100 mol % of all end-groups of the hyperbranched polymer having dimethylamino end-groups are dimethylamino end-groups and more preferably such that 70-100 mol % of all end-groups are dimethylamino end-groups.

The term "end-groups" as used according to the present invention generally refers to the groups at the periphery of the hyperbranched polymer. However, due to the complex structure of hyperbranched polymers such groups may also be sometimes located within the polymer.

In all embodiments of the present invention, the degree of quaternization of the dimethylamino end-groups is preferably selected in the range of 50 to 100 mol-%, more preferably in the range of 70 to 100 mol-%, most preferably in the range of 80 to 100 mol-% and in particular in the range of 85 to 100 mol-%.

It is well understood in the context of the present invention that instead of 2-dodecen-1-ylsuccinic anhydride, the respective di-acid i.e. 2-dodecen-1-yl succinic acid or a mixture of the anhydride and the di-acid can be used. The amounts and ratios given, however, would have to be adjusted accordingly. In all embodiments of the present invention, however, the use of 2-dodecen-1-ylsuccinic anhydride is preferred.

The quaternized hyperbranched polymers according to the present invention may be synthesized as e.g. outlined in WO 2007/098888 A1 or illustrated in the examples of the present invention.

The (theoretical) molecular weight of the hyperbranched polymers (before quaternization) can be adjusted via the ratio of the different building blocks used, in particular by the ratio of diisopropanolamine (branching unit) to 2-dodecen-1-ylsuccinic anhydride which can be easily selected by a person skilled in the art. The effect of N,N-bis[3-(dimethylamino)propyl]amine (chain stopper) on the molecular weight of the resulting polymer can also be calculated by a person skilled in the art.

The ratios are advantageously selected such that the hyperbranched polymers having dimethylamino end-groups exhibit a theoretical (i.e. calculated) average number molecular weight $M_n$ in the range of 1000 to 150,000 g/mol, more advantageously in the range of 1500 to 125,000 g/mol, most preferably in the range of 2000 to 50,000 g/mol and in particular in the range of 2000-4000 g/mol.

Therefore, in all embodiments of the present invention the ratio (w/w) of N,N-bis[3-(dimethylamino)propyl]amine to diisopropanolamine is preferably selected in the range of 4:1 to 0.5:1, more preferably in the range of 3:1 to 1:1. Most preferably N,N-bis[3-(dimethylamino)propyl]amine is used in a molar excess based on diisopropanolamine. Thus, most preferably, the ratio (w/w) of N,N-bis[3-(dimethylamino)propyl]amine to diisopropanolamine is selected in the range of 2.5:1 to 1.2:1, such as in the range of 2.2:1 to 1.2:1.

Also in all embodiments of the present invention, the ratio (w/w) of 2-dodecen-1-ylsuccinic anhydride to the total amount of amines (i.e. N,N-bis[3-(dimethylamino)propyl]amine and diisopropanolamine) is preferably selected in the range of 3:1 to 1:3, preferably in the range of 2:1 to 0.5:1. Most preferably in all embodiments of the present invention, 2-dodecen-1-ylsuccinic anhydride is used in an excess (w/w) based on the total amount of amines (i.e. the sum of N,N-bis[3-(dimethylamino)propyl]amine and diisopropanolamine) such as in a ratio (w/w) selected in the range of 2:1 to 1.2:1.

In a particular advantageous embodiment, the quaternized hyperbranched polymers according to the present invention are obtainable by condensation of 2-dodecen-1-ylsuccinic anhydride, N,N-bis[3-(dimethylamino)propyl]amine and diisopropanolamine followed by complete (i.e. ≥85%) quaternization of the dimethylamino end-groups with sodium 2-chloroacetate, with the proviso that the building blocks for the preparation of the hyperbranched polymer having dimethylamino end-groups are selected in a ratio which is such that a number average molecular weight between 1,500 g/mol and 150,000 g/mol, preferably 1,500 g/mol and 50,000 g/mol is obtained.

The condensation reaction of 2-dodecen-1-ylsuccinic anhydride, diisopropanolamine and N,N-bis[3-(dimethylamino)propyl]amine resulting in hyperbranched polymers having dimethylamino end-groups is advantageously carried out in an one-pot procedure. Preferably, the building blocks are charged stepwise into the reactor, such as e.g. exemplified in WO2007/098888 A1 example 1 to 3. The condensation reaction may be carried out at room temperature or at an elevated temperature. Preferably, the condensation reaction is carried out at a temperature selected in the range of about 100 to 250 C, more preferably in the range of 120 to 200° C. and most preferably in the range of 140 to 180° C. with water being removed, preferably through distillation. The one-pot procedure can take place with or without a solvent. Suitable solvents are organic solvents, such as methylisobutylketone, butylacetate, cyclohexane, methylcyclohexane, toluene or xylene. Preferably, no solvent is used. The removal of water can take place through distillation at reduced pressure, or, alternatively, may be removed azeotropically. Preferably, the water released during the condensation reaction is removed by vacuum (i.e. reduced pressure (<1013 mbar)). The condensation reaction advantageously takes place until >90% by weight, preferably >95% by weight or >98% by weight of the building blocks used are consumed.

The quaternization of the hyperbranched polymer having dimethylamino end groups is generally performed in water or any other suited solvent. Preferably the quaternization is performed in water. Thus, an advantageous process according to the present invention comprises dissolving the hyperbranched polymer having dimethylamino end-groups in water followed by addition of the quaternization reagent and heating the reaction mixture to a temperature selected in the range of 50-120° C. Preferably sodium 2-chloroacetate is used as quaternization reagent. The degree of quaternization depends on the amount of quaternization reagent used and can easily be calculated by a person skilled in the art dependent on the desired degree of quaternization. The ratio (w/w) of water to the hyperbranched polymer having dimethylamino end-groups is advantageously selected in the range 5:1 to 1:5, preferably in the range of 3:1 to 1:2, most preferably in the range of 2:1 to 1:1.

The polymer content of the aqueous solution resulting from the quaternization reaction is frequently 5 to 70 wt.-%, often 20 to 60 wt.-%, or 30 to 50 wt.-% and can be easily adjusted by a person skilled in the art by addition or removal of water.

In a very particular embodiment, the present invention relates to a process for the preparation of hyperbranched polymers according to the present invention said process comprising the step of (a) Forming a hyperbranched polymer having dimethylamino end-groups comprising
  (i) Adding 2-dodecen-1-ylsuccinic anhydride, diisopropanolamine and N,N-bis[3-(dimethylamino)propyl]amine to a reactor followed by
  (ii) Heating the reaction mixture to a temperature of 140-180° C. for about 15-120 minutes followed by
  (iii) Applying vacuum to the reaction to remove the reaction water for about 3-7 hours followed by the step of (b) Quaternization of the dimethylamino end-groups of the hyperbranched polymer obtained in step (a) by reacting said hyperbranched polymer with sodium 2-chloroacetate in water. It is well understood that all the preferences and definitions given above also apply to this process.

The aqueous solution obtained from the quaternization reaction can either be incorporated directly into any aqueous, aqueous-alcoholic or alcoholic cosmetic preparation, such as for example a shampoo preparation, or drying of the solution takes place, e.g. spray-drying or freeze-drying, so that the hyperbranched polymer can be used and processed in the form of the neat polymer.

Preferably, the quaternized hyperbranched polymer according to the present is used as an aqueous solution having a polymer content selected in the range 5 to 70 wt.-%, more preferably in the range of 20 to 60 wt.-% and most preferably in the range of 30 to 50 wt.-%.

The hyperbranched polymers according to the present invention are particularly suited for the formulation of clear shampoo preparations. Thus, in another embodiment the present invention is directed to clear shampoo preparations comprising at least one quaternized hyperbranched polymer according to the present invention.

The term shampoo preparation refers to preparations for cleaning the hair which are to be applied to the hair and then rinsed away.

The amount of the at least one quaternized hyperbranched polymer according to the present invention in the shampoo preparations according to the present invention is preferably selected in the range 0.01-20 wt.-%, more preferably in the range of 0.01-10 wt.-%, most preferably in the range of 0.05-5 wt.-% such as in particular in the range of 0.5 to 2 wt.-% based on the total weight of the shampoo preparation.

The shampoo preparations according to the invention preferably comprise from 50 to 98 wt.-%, more preferably from 60 to 90 wt.-% of water based on the total weight of the shampoo preparation. Furthermore, the shampoo preparations according to the present invention preferably further comprise an anionic surfactant.

Thus, in another preferred embodiment, the present invention relates to clear shampoo preparations comprising next to at least one quaternized hyperbranched polymer according to the present invention water and an anionic surfactant.

The ratio of the anionic surfactant to the quaternized hyperbranched polymer in the shampoo preparations of the present invention is preferably selected in the range of 20 to 1 to 1 to 1, in particular 10 to 1 to 5 to 1, such as in particular 8 to 1.

Exemplary anionic surfactants comprise alkylsulfate, alkylethersulfate, alkylsulfonate, alkylarylsulfonate, alkylsuccinate, alkylsulfosuccinate, N-alkoylsarkosinate, acyltaurate, acyl isethionate, alkylphosphate, alkyletherphosphate, alkylethercarboxylate, alpha-olefinsulfonate, especially the alkali-und earth alkali salts, e.g. sodium, potassium, magnesium, calcium, as well as ammonium- and triethanol amine-salts. The alkylethersulfate, alkyletherphosphate and alkylethercarboxylate may comprise between 1 to 10 ethylenoxide or propylenoxide units, preferably 1 to 3 ethylenoxide-units per molecule. Suitable amionic surfactants are e.g. sodium laurylsulfate, ammonium lauryl sulfate, sodium lauryl ether sulfate (also known as sodium laureth sulfate), ammonium lauryl ether sulfate (also known as ammonium laureth sulfate), sodium lauroylsarkonisate, sodium oleyl succinate, ammonium lauryl sulfosuccinate, sodium dodecylbenzol sulfonate, triethanol amidodecylbenzol sulfonate. Particularly preferred anionic surfactants to be used in the shampoo preparations according to the present invention are sodium lauryl sulfate, ammonium lauryl sulfate, sodium lauryl ether sulfate and ammonium lauryl ether sulfate as well as mixtures thereof.

The total amount of anionic surfactant (as active ingredient) in the shampoo preparations according to the present invention is preferably selected in the range of 0.1 to 50 wt. %, more preferably in the range of 5-20 wt.-% based on the total weight of the shampoo preparation.

The shampoo preparations according to the invention can contain further ingredients to enhance the performance and or consumer acceptability such as preservatives, antioxidants, fatty substances oils, silicones, thickeners, softeners, emulsifiers, light-screening agents, antifoaming agents, moisturizers, fragrances, co-surfactants, fillers, sequestering agents, cationic-, nonionic- or amphoteric polymers or mixtures thereof, acidifying or basifying agents, dyes, colorants, pigments or nanopigments, pearlizers or opacifiers, organic or inorganic particles, viscosity modifiers, and natural hair nutrients such as botanicals, fruit extracts, sugar derivatives and or amino acids or any other ingredients usually formulated into rinse off compositions. The necessary amounts of the adjuvants and additives can, based on the desired product, easily be chosen by a skilled artisan in this field and will be illustrated in the examples, without being limited hereto.

The shampoo preparations according to the present invention preferably include co-surfactants, to help impart aesthetic, physical or cleansing properties to the compositions.

Examples of co-surfactants are nonionic surfactants, which can be included in an amount ranging from 0.5 to 8 wt.-%, preferably from 2 to 5 wt.-% based on the total weight of the preparation. For example, representative nonionic surfactants that can be included into shampoo preparations according to the invention include condensation products of aliphatic ($C_8$-$C_{18}$) primary or secondary linear or branched chain alcohols with alkylene oxides, usually ethylene oxide and generally having from 6 to 30 ethylene oxide groups. Other representative nonionic surfactants include mono- or di-alkyl alkanolamides such as e.g. coco mono- or di-ethanolamide and coco mono-isopropanolamide. Further nonionic surfactants which can be included in shampoo preparations of the invention are the alkyl polyglycosides (APGs). Typically, the APG is one which comprises an alkyl group connected (optionally via a bridging group) to a block of one or more glycosyl groups such as e.g. Oramix NS 10 ex Seppic; Plantacare 818UP, Plantacare 1200 and Plantacare 2000 ex Cognis.

Another example of co-surfactants are amphoteric or zwitterionic surfactants, which can be included in an amount (as active ingredient) ranging from 0.5 to about 8 wt.-%, preferably from 1 to 4 wt.-% based on the total weight of the shampoo preparation. Examples of amphoteric or zwitterionic surfactants include alkyl amine oxides, alkyl betaines, alkyl amidopropyl betaines, alkyl sulphobetaines (sultaines), alkyl glycinates, alkyl carboxyglycinates, alkyl amphoacetates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoo preparations according to the present invention include lauryl amine oxide, cocodimethyl sulphopropyl betaine, lauryl betaine, cocamidopropyl betaine (CAPB), sodium cocoamphoacetate and disodium cocoamphodiacetate. Particularly preferred amphoteric or zwitterionic surfactant to be used in the shampoo preparations of the present invention are cocamidopropyl betaine and disodium cocoamphodiacetate as well as a mixture thereof.

Thus, in a further advantageous embodiment the invention relates to clear shampoo preparations comprising at least one quaternized hyperbranched polymer according to the present invention, further comprising water, an anionic surfactant and an amphoteric or zwitterionic surfactant.

In an even more advantageous embodiment, the anionic surfactant is selected from the group consisting of sodium lauryl sulfate, ammonium lauryl sulfate, sodium lauryl ether sulfate and ammonium lauryl ether sulfate as well as mixtures thereof and the amphoteric or zwitterionic surfactant is selected from cocamidopropyl betaine and disodium cocoamphodiacetate as well as a mixture thereof.

In a particular preferred embodiment, the shampoo preparations according to the present invention only contain anionic surfactants selected from the group consisting of sodium lauryl sulfate, ammonium lauryl sulfate, sodium lauryl ether sulfate and ammonium lauryl ether sulfate as well as mixtures thereof and amphoteric or zwitterionic surfactants selected from cocamidopropyl betaine and disodium cocoamphodiacetate as well as mixtures thereof as surfactants.

In all embodiments of the present invention, the total amount of surfactants (including any co-surfactants based on active content) in the shampoo preparations according to invention is generally selected in the range of 1 to 50 wt.-%, preferably in the range of 2 to 40 wt.-%, more preferably in the range of 5 to 25 wt.-%, such as in particular in the range of 9 to 15 wt.-% based on the total weight of the shampoo preparation.

The compositions according to the invention may also comprise a hydrotrope. A hydrotrope is a substance that improves the solubility of surfactants in water. Examples of hydrotropes are sodium xylene sulfonate, ammonium xylene sulphonate, sodium p-toluene sulfonate, sodium chlorobenzene sulfonate, sodium salicylate, proline, pyrogallol, resorcinol and urea. If used, preferably sodium xylene sulfonate is used as hydrotrope. The total amount of the hydrotrope in the shampoo preparations according to the invention preferably ranges from 0.5 to 30 wt.-%, preferably from 1 to 20 wt.-%, in particular from 1 to 5 wt.-% based on the total weight of the shampoo preparation.

The shampoo preparations according to the invention may also contain further cationic polymers. Suitable cationic polymers may be homopolymers which are cationically substituted or may be formed from two or more types of monomers. The weight average molecular weight (Mw) of the polymers will generally be between 100 000 and 2 million Daltons. Suitable cationic polymers include, for example, copolymers of vinyl monomers having cationic amine or quaternary ammonium functionalities with water soluble spacer monomers such as (meth) acrylamide, alkyl and dialkyl (meth) acrylamides, alkyl (meth) acrylate, vinyl caprolactone and vinyl pyrrolidine. The alkyl and dialkyl substituted monomers preferably have $C_1$-$C_7$ alkyl groups, more preferably $C_{1-3}$ alkyl groups. Other suitable spacers include vinyl esters, vinyl alcohol, maleic anhydride, propylene glycol and ethylene glycol.

Suitable cationic polymers for use in the shampoo preparations according to the present invention include, for example:
  cationic diallyl quaternary ammonium-containing polymers including, for example, dimethyldiallylammonium chloride homopolymer and copolymers of acrylamide and dimethyldiallylammonium chloride, referred to in the industry (CTFA) as Polyquaternium 6 and Polyquaternium 7, respectively;
  mineral acid salts of amino-alkyl esters of homo- and co-polymers of unsaturated carboxylic acids having from 3 to 5 carbon atoms, (as described in U.S. Pat. No. 4,009,256)
  cationic polyacrylamides (as described in WO95/22311).

Other cationic polymers that can be used include cationic polysaccharide polymers, such as cationic cellulose derivatives, cationic starch derivatives, and cationic guar gum derivatives.

Cationic cellulose derivatives includes the polymeric quaternary ammonium salts of hydroxyethyl cellulose reacted with trimethyl or lauryl dimethyl ammonium-substituted epoxide, referred to in the industry (CTFA) as Polyquaternium-10 and Polyquaternium-24 respectively. These materials are available from the Amerchol Corporation, for instance under the trade name Ucare Polymer JR or Ucare Polymer LM.

Suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581). A particularly suitable type of cationic polysaccharide polymer that can be used is a cationic guar gum derivative, such as guar hydroxypropyltrimethylammonium chloride or hydroxypropyl guar hydroxypropyltrimethylammonium chloride (commercially available from Rhodia in their JAGUAR trademark series). Examples of such materials are JAGUAR C135, JAGUAR C145, JAGUAR C17; JAGUAR C162 and JAGUAR Excel.

Mixtures of any of the above cationic polymers may be used.

If used, the total amount of the further cationic polymer(s) is preferably selected in the range of 0.01 to 5 wt.-%, more preferably in the range of 0.05 to 1 wt.-%, and most preferably in the range of 0.08 to 0.5 wt.-% based on the total weight of the shampoo preparation.

The shampoo preparations of the invention may further comprise a suspending agent. Suitable suspending agents are selected from cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives, since these impart pearlescence to the composition. Polymers of acrylic acid cross-linked with a polyfunctional agent may also be used; they are available commercially as Carbopol 910, Carbopol 934, Carbopol 941, Carbopol 980 and Carbopol Ultrez 10 Polymer. Examples of suitable copolymers of a carboxylic acid containing monomer and acrylic acid esters are Carbopol 1342, Carbopol Ultrez 20 or Carbopol Ultrez 21, Pemulen TR1 or Pemulen TR2. All Carbopol or Pemulen (trademark) materials are available from Noveon Consumer Specialities.

A suitable heteropolysaccharide gum is xanthan gum, for example Keltrol-types or Kelzan-types from Kelco, Vanzan NF from RT Vanderbilt Inc. or Rhodicare-types from Rhodia.

Mixtures of any of the above suspending agents may be used. Preferred is a mixture of cross-linked polymer of acrylic acid and crystalline long chain acyl derivative.

If present, the total amount of the suspending agent(s) is preferably selected in the range of 0.1 to 10 wt.-%, more preferably in the range of 0.5 to 6 wt.-%, most preferably in the range of 0.9 to 4 wt.-% based on the total weight of the composition.

The shampoo preparations of the invention may comprise further conditioning agents to further optimize wet and dry conditioning benefits.

Particularly preferred further conditioning agents are silicone emulsions. Suitable silicone emulsions include those formed from silicones such as polydiorganosiloxanes, in particular polydimethylsiloxanes which have the CTFA designation dimethicone, polydimethyl siloxanes having hydroxyl end-groups which have the CTFA designation dimethiconol, and amino-functional polydimethyl siloxanes which have the CTFA designation amodimethicone. Suitable silicone emulsions for use in compositions of the invention are available from suppliers of silicones such as Dow Corning, Momentive Performance Materials, KCC or Wacker.

If used, the total amount of silicone(s) (as active) is preferably selected in the range of 0.05 to 10 wt.-%, more preferably in the range of 0.05 to 5 wt.-%, most preferably in the range of 0.5 to 2 wt.-% based on the total weight of the shampoo preparation.

The shampoo preparations according to the invention may further contain anti dandruff agents. Examples of anti-dandruff agents which may be used are cimbazole, octopirox and zinc pyrithione. Customary film formers include, for example, chitosan, microcrystalline chitosan, quaternized chitosan, polyvinylpyrrolidone, vinyl pyrrolidone vinyl acetate copolymers, polymers of quaternary cellulose derivatives containing a high proportion of acrylic acid, collagen, hyaluronic acid and salts thereof and similar compounds.

The shampoo preparations according to the invention may further contain UV-filter substances. Examples of UV-filter substances suitable for the incorporation into the compositions according to the invention include benzophenones such as e.g. benzophenones-4 or benzophenones-3, acrylates such as 2-ethylhexyl 2-cyano-3,3-diphenylacrylate (octocrylene, PARSOL® 340), cinnamate derivatives such as ethylhexyl methoxycinnamate (PARSOL® MCX), benzalmalonate derivatives bond to siloxanes such as e.g. polysilicones-15 (PARSOL® SLX), salicylate derivatives such as isopropylbenzyl salicylate, benzyl salicylate, butyl salicylate, ethylhexyl salicylate (PARSOL® EHS, Neo Heliopan OS), isooctyl salicylate or homomenthyl salicylate (homosalate, PARSOL® HMS, Neo Heliopan HMS), benzotriazole derivatives such as sodium benzotriazolyl butylphenol sulfonate, imidazole derivatives such as e.g. 2-phenyl benzimidazole sulfonic acid and its salts (PARSOL® HS), dibenzoylmethane derivatives such as (avobenzone, Parsol® 1789) without being limited thereto.

The invention is further illustrated with reference to the following, non-limiting examples, in which all percentages are by weight based on total weight unless otherwise specified.

EXAMPLE 1

Preparation of Polymer Samples

A. Hyperbranched Polymer Having Dimethylamine End-Groups 232 g of N,N-bis[3-(dimethylamino)propyl]amine and 109.9 g molten diisopropanolamine were added to a glass reactor equipped with stirrer and condenser, and which can be heated by oil. To this mixture 458.1 g of molten 2-dodecen-1-ylsuccinic anhydride was added. After addition the mixture was slowly heated to 160° C. and 1 h later vacuum was applied to remove the reaction water. After 5 h the mixture was cooled and a viscous polymer was obtained.

EXAMPLE A1

Methyl-Quaternised Hyperbranched Polymer (Reference)

50 g of the hyperbranched polymer having dimethylamine endgroups of example 1 was dissolved in 67.6 g water and at room temperature 17.6 g of dimethyl sulfate (DMS) was slowly added. First the mixture was turbid but within 10 min the temperature raised to about 50° C. and the mixture became clear. After 24 h the quaternized polymer solution was ready for use. Calculated level of quaternized dimethylamino end-groups: 90%.

EXAMPLE A2

Protonised Hyperbranched Polymer (Reference)

50 g of the hyperbranched polymer having dimethylamine endgroups of example 1 was dissolved in 63.4 g water and at room temperature 13.4 g of methane sulfonic acid (MeSA) was slowly added and completely mixed with the polymer-water mixture after which the protonised polymer solution was ready for use. Calculated level of protonisation of dimethylamino end-groups: 90%.

EXAMPLE A3

Hyperbranched Polymer According to the Present Invention 50 g of the hyperbranched polymer having dimethylamine endgroups of example 1 was dissolved in 66.3 g water and to this mixture 16.3 g sodium 2-chloroacetate (SMCA) was added. This mixture was reacted at 80° C. for approximately 10 hours while stirring after which the quaternized polymer solution was ready for use. Calculated level of quaternized dimethylamino end-groups: 90%. Color: slightly yellowish.

In analogy to Example 1 further hyperbranched polymers have been prepared exhibiting different $M_n$. The respective quaternized samples have also been prepared in analogy to the methods described in examples A1, A2 and A3. The respective amounts of raw materials used are given in table 1.

TABLE 1

Summary of hyperbranched polymers prepared

| Example No. | $Mn^\#$ [g/mol] | BDMAPA | DiPA [g]* | DDSA | HHPA | DMS | MeSA [g]** | SMCA |
|---|---|---|---|---|---|---|---|---|
| A1 (Ref.) | 2200 | 232 | 109.9 | 458.1 | — | 17.6 | — | — |
| A2 (Ref) | 2200 | 232 | 109.9 | 458.1 | — | — | 13.4 | — |
| A3 (Inv) | 2200 | 232 | 109.9 | 458.1 | — | — | — | 16.3 |
| B1 (Ref) | 17000 | 181.8 | 123.7 | 494.5 | — | 13.9 | — | — |
| B2 (Ref) | 17000 | 181.8 | 123.7 | 494.5 | — | — | 10.6 | — |
| B3 (Inv) | 17000 | 181.8 | 123.7 | 494.5 | — | — | — | 12.8 |
| C1 (Ref) | 33000 | 176.7 | 125.9 | 497.4 | — | 13.6 | — | — |
| C2 (Ref) | 33000 | 176.7 | 125.9 | 497.4 | — | — | 10.3 | — |
| C3 (Inv) | 33000 | 176.7 | 125.9 | 497.4 | — | — | — | 12.5 |
| D1 (Ref) | 121000 | 172.4 | 127.9 | 499.7 | — | 13.0 | — | — |
| D2 (Ref) | 121000 | 172.4 | 127.9 | 499.7 | — | — | 9.9 | — |
| D3 (Inv) | 121000 | 172.4 | 127.9 | 499.7 | — | — | — | 12.0 |
| E1 (Ref) | 1700 | 305.4 | 145.0 | 0 | 349.7 | 21.3 | — | — |
| E2 (Ref) | 1700 | 305.4 | 145.0 | 0 | 349.7 | — | 16.2 | — |
| E3 (Ref) | 1700 | 305.4 | 145.0 | 0 | 349.7 | — | — | 19.7 |

BDMAPA: N,N-bis[3-(dimethylamino)propyl]amine
DiPA = Diisopropanolamine
DDSA = 2-Dodecen-1-ylsuccinic anhydride
HHPA = Hexahydrophthalic anhydride
SMCA = Sodium 2-chloroacetate
DMS = Dimethylsulfate
MeSA = Methylsulfonic acid
$^\#$calculated Mn of the non-quaternized hyperbranched polymer having dimethylamino end-groups
*weight based on 800 g reactor filling
**weights based on 50 g hyperbranched polymer having dimethylamine endgroups.

EXAMPLE 2

Influence of Polymer on the Turbidity of a Shampoo Preparation

A standard shampoo preparation as outlined in table 1 was prepared using different polymer samples of Example 1. Afterwards the turbidity of the shampoo was assessed visually. The results are illustrated in table 3.

TABLE 2

Standard Shampoo preparation

| Ingredient (INCI) | Wt.-% |
|---|---|
| Polymer | See table 3 |
| Sodium Laureth Sulfate 28%/Water 72% | 35.0% |
| Cocamidopropyl Betaine 40%/Water 60% | 5.0% |
| Sodium Benzoate | 0.5% |
| Citric acid | 0.1% |
| Sodium Chloride | See table 3 |
| Water | Ad 100 |

The pH of the shampoos was in the range of 4.5-5.5

TABLE 3

Results of the turbidity assessment of the shampoo preparations

| Polymer | Polymer [wt.-%] | NaCl [wt.-%] | Visual appearance of respective shampoo preparation |
|---|---|---|---|
| A3 | 0.5 | 1.5 | clear |
| A3 | 1.0 | 1.5 | clear |
| A3 | 2.0 | 1.5 | clear |
| B3 | 1.0 | 1.0 | clear |
| B2 (Ref) | 1.0 | 1.0 | turbid |
| B1 (Ref) | 1.0 | 1.0 | turbid |
| C3 | 1.0 | 1.5 | clear |
| C3 | 0.50 | 1.5 | clear |
| C2 (Ref) | 1.0 | 1.2 | turbid |
| C2 (Ref) | 0.5 | 1.5 | turbid |
| C1 (Ref) | 1.0 | 1.0 | turbid |
| C1 (Ref) | 0.5 | 1.5 | turbid |
| D3 | 0.5 | 1.5 | clear |
| D2 (Ref) | 0.5 | 1.5 | turbid |
| D1 (Ref) | 0.5 | 1.5 | turbid |

As can be retrieved from table 3 only the polymers quaternized with sodium 2-chloroacetate resulted in clear shampoo preparations in a broad concentration range whereas the polymers quaternized with dimethylsulfate or protonated resulted in turbid shampoo preparations.

EXAMPLE 3

Influence of Polymer on the Viscosity of a Shampoo Preparation

The polymers A1, A3, E2 and E3 of example 1 built up from different anhydride building blocks and quaternized either with SMCA, DMS or protonated with MeSAP have been incorporated into a standard shampoo formulation outlined in table 4, in the amounts indicated in table 5. The viscosities of the respective shampoos were determined with a Brookfield Rheometer RVT, Spindle 4 at 10 rpm at 22° C. For shampoos exhibiting already a low viscosity at low concentrations of polymer higher concentrations have not always been tested as an increased amount of polymer anyway results in a further decrease of the viscosity.

TABLE 4

Standard Shampoo

| Ingredient (INCI) | Wt.-% |
|---|---|
| Polymer | See table 5 |
| Sodium Laureth Sulfate 28%/Water 72% | 35.0 |
| Cocamidopropyl Betaine 40%/Water 60% | 5.0 |
| Sodium Benzoate | 0.5 |
| Citric acid | 0.1 |
| Sodium Chloride | 1.5 |
| Water | q.a. |

The pH of the formulation was in the range of 3.5-5

TABLE 5

Results of the viscosity assessment of the shampoo preparations

| Polymer | Quaternisation | Anhydride building block | Amount [wt.-%] | Viscosity [mPas] | Product form |
|---|---|---|---|---|---|
| A3 (inventive) | SMCA | DDSA | 5 | 16000 | Good |
| A3 (inventive) | SMCA | DDSA | 2 | 18000 | Good |
| A3 (inventive) | SMCA | DDSA | 1 | 19000 | Good |
| A1 (Reference) | DMS | DDSA | 2 | 840 | Too liquid |
| A1 (Reference) | DMS | DDSA | 0.5 | 1080 | Too liquid |
| E2 (Reference) | MeSAP | HHPA | 2 | 1020 | Too liquid |
| E2 (Reference) | MeSAP | HHPA | 0.5 | 1280 | Too liquid |
| E3 (Reference) | SMCA | HHPA | 5 | 200 | Too liquid |
| E3 (Reference) | SMCA | HHPA | 2 | 500 | Too liquid |
| E3 (Reference) | SMCA | HHPA | 1 | 700 | Too liquid |

As can be retrieved from the results of the examples presented in table 3 and 5 only the use of polymers according to the present invention built up with 2-dodecen-1-ylsuccinic anhydride as anhydride building block and which are quaternized with sodium 2-chloroacetate result in clear shampoo formulation with acceptable viscosities.

The invention claimed is:

1. A quaternized hyperbranched polymer having end-groups of formula (I):

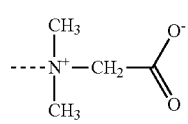

wherein the quaternized hyperbranched polymer is a condensation reaction product of a reaction mixture consisting of:
(i) 2-dodecen-1-ylsuccinic anhydride,
(ii) diisopropanolamine, and
(iii) N,N bis[3-(dimethylamino)propyl]amine,
to obtain a hyperbranched polymer having dimethylamino end groups followed by quaternization of the dimethylamino end-groups to end groups of formula (I).

2. The quaternized hyperbranched polymer according to claim 1, wherein the quaternized hyperbranched polymer having dimethylamino end-groups is the condensation reaction product of a reaction mixture consisting of:
(i) 40-70 wt.-% of 2 dodecen-1-ylsuccinic anhydride,
(ii) 5-20 wt.-% of diisopropanolamine, and
(iii) 15-45 wt.-% of N,N-bis[3-(dimethylamino)propyl] amine, wherein
the 2 dodecen-1-ylsuccinic anhydride, the diisopropanolamine and the N,N-bis[3-(dimethylamino)propyl] amine are present in a total amount which sums to 100 wt.-%.

3. The quaternized hyperbranched polymer according to claim 1, wherein the dimethylamino end-groups are quaternized with sodium 2 chloroacetate.

4. The quaternized hyperbranched polymer according to claim 1, wherein the degree of quaternization of the dimethylamino end-groups is in a range of 50 to 100 mol-%.

5. The quaternized hyperbranched polymer according to claim 1, wherein a ratio (w/w) of N,N-bis[3-(dimethylamino)propyl]amine to diisopropanolamine is in a range of 4:1 to 0.5:1.

6. The quaternized hyperbranched polymer according to claim 5, wherein the ratio (w/w) of N,N-bis[3-(dimethylamino)propyl]-amine to diisopropanolamine is in the range of 2:5 to 1.2:1.

7. The quaternized hyperbranched polymer according to claim 1, wherein a ratio (w/w) of 2-dodecen-1-ylsuccinic anhydride to the total amount of amines is in a range of 3:1 to 1:3.

8. The quaternized hyperbranched polymer according to claim 1, wherein the hyperbranched polymer having dimethylamino end-groups has an average number molecular weight Mn which is in a range of 1,000 to 150,000 g/mol.

9. The quaternized hyperbranched polymer according to claim 1, wherein the quaternized hyperbranched polymer is in the form of an aqueous solution comprising 30-50 wt.-% of the quaternized hyperbranched polymer, based on polymer content in the aqueous solution.

10. A clear shampoo preparation comprising a hyperbranched polymer according to claim 1.

11. The clear shampoo preparation according to claim 10, wherein the hyperbranched polymer is present in an amount within a range of 0.01-20 wt. %, based on total weight of the shampoo preparation.

12. The clear shampoo preparation according to claim 10, which further comprises water, an anionic surfactant and an amphoteric or zwitterionic surfactant.

13. The clear shampoo preparation according to claim 12, wherein the anionic surfactant is selected from the group consisting of sodium lauryl sulfate, ammonium lauryl sulfate, sodium lauryl ether sulfate, ammonium lauryl ether sulfate and mixtures thereof, and wherein the amphoteric or zwitterionic surfactant is selected from the group consisting of cocamidopropyl betaine, disodium cocoamphodiacetate and mixtures thereof.

14. The clear shampoo preparation according to claim 12, wherein the anionic surfactant and the amphoteric or zwitterionic surfactant are present in a total amount in the range of 1 to 50 wt. %, based on the total weight of the shampoo preparation.

15. The clear shampoo preparation according to claim 12, wherein the anionic surfactant and the hyperbranched polymer are present in a ratio of the anionic surfactant to the hyperbranched polymer in a range of 10 to 1 to 5 to 1.

16. A process for the preparation of a hyperbranched polymer having end-groups of formula (I):

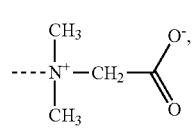 (I)

wherein
the process comprises the steps of:
(a) subjecting a reaction mixture consisting of (i) 2 dodecen-1-ylsuccinic anhydride, (ii) diisopropanolamine, and (iii) N,N bis[3-(dimethylamino)propyl]amine to condensation reaction conditions to form a hyperbranched polymer having dimethylamino end-groups, followed by
(b) quaternization of the dimethylamino end-groups of the hyperbranched polymer to obtain a hyperbranched polymer with the end groups of formula (I).

* * * * *